United States Patent [19]

Traveset-Masanes et al.

[11] Patent Number: 5,324,427
[45] Date of Patent: Jun. 28, 1994

[54] COUPLING ARRANGEMENT FOR CHROMATOGRAPHY COLUMNS

[75] Inventors: Jordi Traveset-Masanes; Rodolfo Zaplana-Cunillera; Vicente Such-Quintana, all of San Cugat del Valles, Spain

[73] Assignee: Tracer Analitica S.L., Barcelona, Spain

[21] Appl. No.: 51,194

[22] Filed: Apr. 22, 1993

[51] Int. Cl.⁵ .............................................. B01D 15/08
[52] U.S. Cl. .................... 210/198.2; 210/656; 96/101
[58] Field of Search .................. 210/656, 198.2, 232, 210/238; 55/386; 96/101; 422/70

[56] References Cited

U.S. PATENT DOCUMENTS

| | | | |
|---|---|---|---|
| 3,904,527 | 9/1975 | Wilhelmson | 210/198.2 |
| 4,026,803 | 5/1977 | Abrahams et al. | 210/198.2 |
| 4,283,280 | 8/1981 | Brownlee | 210/198.2 |
| 4,313,828 | 2/1982 | Brownlee | 210/198.2 |
| 4,366,945 | 1/1983 | Blauenstein | 251/149.6 |
| 4,399,032 | 8/1983 | Mott | 210/198.2 |
| 4,451,364 | 5/1984 | Higgins | 210/198.2 |
| 4,478,715 | 10/1984 | Goodnight | 210/198.2 |
| 4,563,275 | 1/1986 | McEachern | 210/198.2 |
| 4,636,316 | 1/1987 | Harris et al. | 210/198.2 |
| 4,655,917 | 4/1987 | Shackelford | 210/198.2 |
| 4,719,011 | 1/1988 | Shalon | 210/198.2 |
| 4,737,284 | 4/1988 | Hauke | 210/198.2 |
| 4,758,340 | 7/1988 | Marchand | 210/198.2 |
| 4,769,141 | 9/1988 | Couillard | 210/198.2 |
| 4,806,238 | 2/1989 | Sattler | 210/198.2 |
| 4,861,473 | 8/1989 | Shackelford | 210/198.2 |
| 4,874,520 | 10/1989 | Lee | 210/198.2 |
| 4,876,005 | 10/1989 | America | 210/198.2 |

FOREIGN PATENT DOCUMENTS

| | | | |
|---|---|---|---|
| 1598506 | 2/1971 | Fed. Rep. of Germany | 210/198.2 |
| 3313257 | 10/1984 | Fed. Rep. of Germany | 210/198.2 |
| 8605918.1 | 4/1986 | Fed. Rep. of Germany | 210/198.2 |

Primary Examiner—Ernest G. Therkorn
Attorney, Agent, or Firm—Birch, Stewart, Kolasch & Birch

[57] ABSTRACT

The invention relates to a coupling arrangement for columns without the need for any ancillary tools. The arrangement includes receptors for spheres placed at various levels to allow a precolumn to be optionally included.

4 Claims, 2 Drawing Sheets

COUPLING ARRANGEMENT FOR CHROMATOGRAPHY COLUMNS

DESCRIPTION

The present invention relates to a new fixing arrangement for chromatography columns.

The high-pressure fluid chromatography columns presently comprise an inner-polished steel pipe with a nipple at each of the pipe ends.

These nipples incorporate a microfilter which function is to retain the filling microparticles and which microfilter packaged at high pressure inside said assembly suitably makes up the proper chromatographic substrate accountable for the analytical separation.

This analytical separation is achieved by pumping a suitable solvent through the chromatographic column, and taking into account the high loading losses caused by these microparticulate fillings (3–10 um), it will then be required to work at pressures which might easily reach a range of 3000–4000 psi.

The new chromatography column system which is, object of the present invention, provides as regards the above disclosed present state of the art, the advantages as listed below.

1. If an extended use of the column causes the chromatographic filling to be exhausted it will then only be required to replace the steel pipe containing the filling with a new one, and the column's input and output nipples become thereby reusable contrary to the present case where the total system both nipples and column is disposed of. The advantage provided by the inventive arrangement yields remarkable savings for the user.

2. In the replacement of any old cartridge by another new one, no tool will be required since a quick-coupling arrangement has particularly been designed for the chromatographic cartridge.

3. The concept of the new cartridge-nipple arrangement allows, without requiring any additional fittings, that a cartridge acting as a pre-column can be inwardly coupled there, with the beneficial purpose of lengthening the column's useful life.

4. The design of the new pre-column cartridge-coupling arrangement eliminates the formation of dead volumes, the presence of which might be very critical for any chromatographic separation.

The above objects are achieved because the new design fully removes any requirement of coupling fittings between both components.

To facilitate still further the disclosure, the present description is accompanied by drawing sheets, wherein a case of embodiment cited only by way of example is illustratively shown.

DESCRIPTION OF THE PREFERRED EMBODIMENT

Returning to the figures, the embodiment of a new fixing arrangement for chromatography columns can be seen a first means designed to retain the column, 1, a second means designed to fix and hermetically seal the connecting nipple, 7.

The column's retaining means are made up with blind housings, 13 and 14, provided at the column's outside surface and placed at a different level and designed to receive respective spheres, 15, located at through-holes drilled in the wall of a column's coaxially tubular body, 2, provided with a likely-inverted vessel concentrically wall, 2A, which combined with a releasing/retaining bushing, 3, sets up a housing for a compressing spring 5, which function by moving along said bushing, 3 towards an operating position, only limited by a safety ring, 4, which keeps the assembly duly joined and at which operating position, the axial stress against the spheres, 15, is laid down.

The change of the column, 1, is performed without the help of any special tools and exclusively only by means of the body, 2, providing the column's quick change by simply axially moving along said body, 2, until the blind holes, 16, drilled in the body's inner surface are mated with the spheres, 15.

The fixing means of the connecting nipple, 7, comprise a knurled nut, 6, allowing said nipple, 7, to be fixed to the column, 1, both manually through its outside knurling and by means of a wrench through its fixing planes.

Said unit is associated to the body, 2, by the threaded portion, 2b, provided thereon, and the nipple, 7, is fixed in cooperation with the radial wing, 7b.

Figure 1:
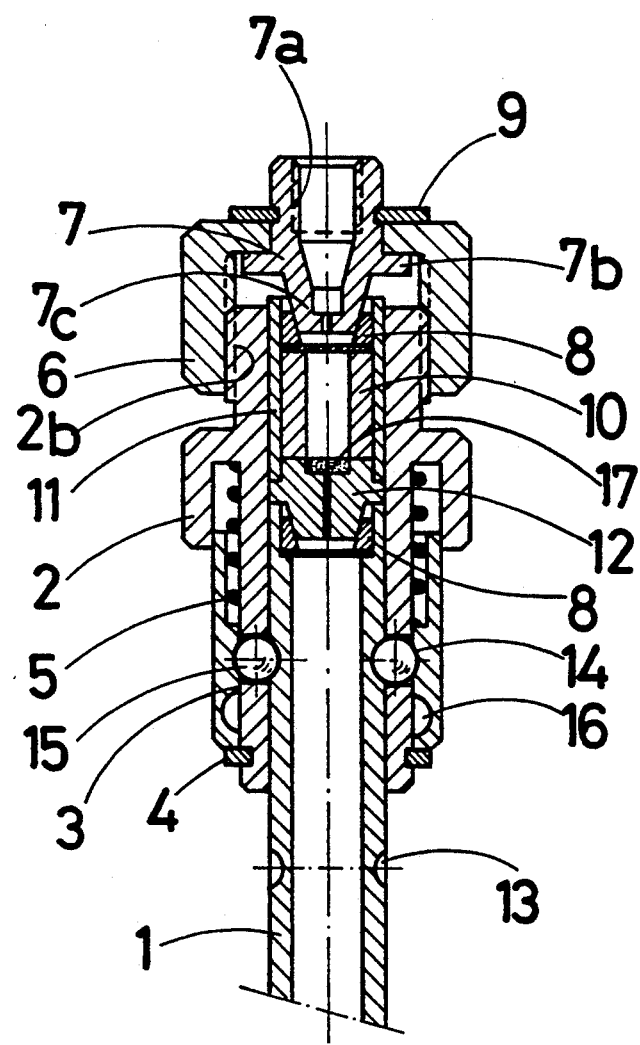
FIG. 1 shows a diametral cross-section of a chromatographic column, wherein said column's retaining means and the connecting nipple's hermetically sealed fixing means can be seen, including a cartridge acting as a pre-column.
Figure 2:
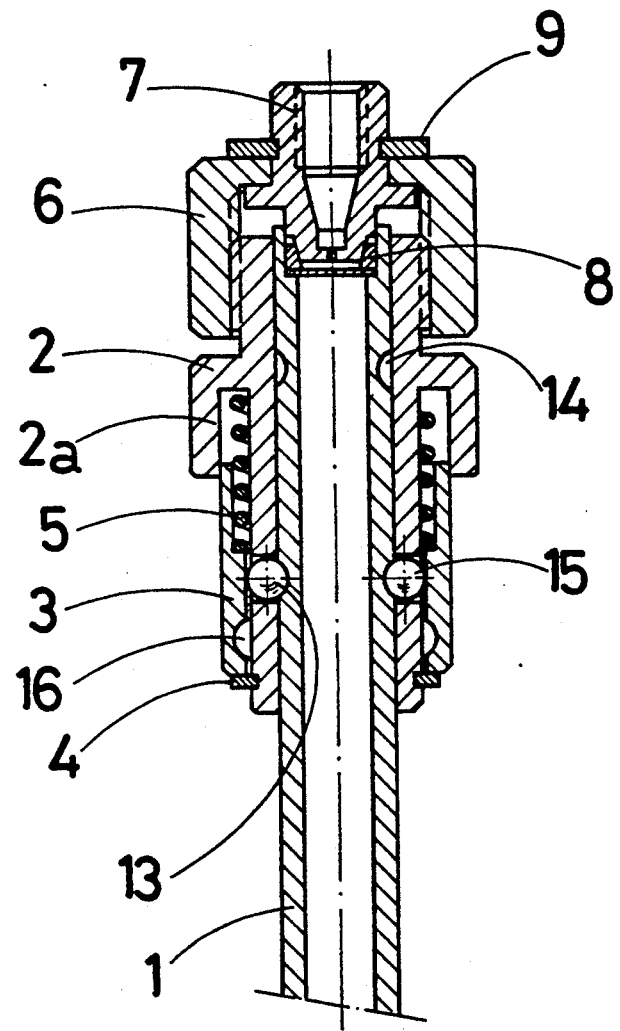
FIG. 2 shows a view similar to the previous one, wherein the arrangement, object of the present invention, is shown when the pre-column cartridge is excluded.

The connecting nipple, 7, has an inner thread, 7a, to fix the capillary and a male cone so that hermetic sealing of the gasket, 8, fitted at the pre-column cartridge, 10, as seen in the FIG. 1 or at the column, 1 as seen in the FIG. 2, can be achieved, all that to receive the axial stress of the nipple's cone, 7c as performed by the nut, 6.

The pre-column cartridge, 10, is housed in the lining, 11 supporting the cartridge and the sealing components.

A part, 12, incorporating a filter component, 17, makes a connection with the column, 1.

The blind holes 13 and 14, allow the pre-column cartridge, 10, to be included or not, as required.

We claim:

1. A coupling arrangement for chromatography columns comprising a first column with input and output nipples and retaining means designed to allow a manual quick change, without any ancilliary tools and facilitating the reuse of the column's input and output nipples and a second means designed to couple and hermetically seal the connecting nipple in the fixing of the capillary, wherein in FIGS. 1 and 2, said first means has blind holes, 13 and 14, located at the outside surface of the column, 1, and placed at different levels are receptors of spheres, 15, retained in holes drilled in the column's coaxially tubular body, 2, provided with a similarly-inverted vessel concentric annular wall, 2a, which combined with a bushing, 3, directed toward a column retaining operating position through a compression means, 5, is susceptible to being moved toward an inactive or releasing position of said column, determined by the presence of blind holes, 16, provided at the inner surface of the bushing, 3.

2. The coupling arrangement for chromatography columns, according to claim 1, wherein said blind holes, 13 and 14, allow a pre-column cartridge, 10, to be included or not, while its presence contributes to the column useful life.

3. The coupling arrangement for chromatography columns, according to claims 1 or 2 wherein the coupling means of a connecting nipple, 7, are made up with a threaded portion, 2b, provided at the end of the body, 2, combined with a nut, 6, which retains said nipple at the radial wing, 7b, said nipple showing a portion axially arisen with an inner thread, 7a, to fix the capillary and a male cone, so that hermetic sealing of a gasket, 8, housed in the pre-column cartridge, 10, or directly at the column, 1, can be assured.

4. The coupling arrangement for chromatography columns according to claim 1, wherein said compression means is a spring.

* * * * *